(12) United States Patent
Wu et al.

(10) Patent No.: US 10,322,177 B2
(45) Date of Patent: Jun. 18, 2019

(54) ACTIVATION OF IMMUNE-RELATED SIGNALING PATHWAYS IN CELLS VIA OPTOFECTION

(71) Applicant: Nant Holdings IP, LLC, Culver City, CA (US)

(72) Inventors: Ting Wu, Culver City, CA (US); Kayvan Niazi, Encino, CA (US)

(73) Assignee: NANT HOLDINGS IP, LLC, Culver City, CA (US)

( * ) Notice: Subject to any disclaimer, the term of this patent is extended or adjusted under 35 U.S.C. 154(b) by 0 days.

(21) Appl. No.: 15/288,910

(22) Filed: Oct. 7, 2016

(65) Prior Publication Data

US 2017/0100479 A1    Apr. 13, 2017

Related U.S. Application Data

(60) Provisional application No. 62/238,652, filed on Oct. 7, 2015.

(51) Int. Cl.
  A61K 41/00    (2006.01)
  A61K 31/708   (2006.01)
  A61K 38/05    (2006.01)

(52) U.S. Cl.
  CPC ........... *A61K 41/00* (2013.01); *A61K 31/708* (2013.01); *A61K 38/05* (2013.01); *A61K 41/0028* (2013.01)

(58) Field of Classification Search
  None
  See application file for complete search history.

(56) References Cited

U.S. PATENT DOCUMENTS

| 8,932,575 | B2 | 1/2015 | Stone |
| 2011/0111002 | A1 | 5/2011 | Pop |
| 2013/0039933 | A1 | 2/2013 | Barber |
| 2013/0039942 | A1 | 2/2013 | Kombluth et al. |
| 2013/0113140 | A1 | 5/2013 | Gunn-Moore et al. |
| 2014/0329889 | A1 | 11/2014 | Vance et al. |
| 2015/0159136 | A1 | 6/2015 | Stone |
| 2015/0252080 | A1 | 9/2015 | Stone et al. |

FOREIGN PATENT DOCUMENTS

| CN | 102776237 A | 11/2012 |
| CN | 103908468 A | 7/2014 |
| EP | 2550298 B1 | 7/2015 |
| EP | 2892930 A1 | 7/2015 |
| WO | 2016096174 A1 | 6/2016 |

OTHER PUBLICATIONS

Yao, et al. (Oct. 10, 2009) "Laser-based transfection with conjugated gold nanoparticles", Chinese Optic Letters, 7(10): 898-900.*
Koelsch, et al. (Apr. 2013) "GFP Affects Human T cell Activation and Cytokine Production following In Vitro Stimulation", PLoS one, 8(4) e50068, 6 pages long.*
Spector, et al. (2010) "Transfection of Mammalian Cells with Fluorescent Protein Fusions", Cold Spring Harbor Protocols, doi: 10.1101/pdb.prot4449, 1233-37.*
Jin, et al. (Aug. 2011) "MPYS Is Required for IFN Response Factor 3 Activation and Type I IFN Production in the Response of Cultured Phagocytes to Bacterial Second Messengers Cyclic-di-AMP and Cyclic-di-GMP" Journal of Immunology, 187(9): 2595-2601.*
McManus, et al. (2002) "Small Interfering RNA-Mediated Gene Silencing in T Lymphocytes", The Journal of Immunology, 169(10): 5754-60.*
Vargas, et al. (2017) "Rationale for stimulator of interferon genes-targeted cancer immunotherapy", European Journal of Cancer, 75 : 86-97.*
Caruso, et al. (2014) "NOD1 and NOD2: Signaling, Host Defense, and Inflammatory Disease", Immunity, 41(6): 898-908.*
https://en.wiktionary.org/wiki/neoepitope, Author unknown, published online by Wikimedia, San Francisco, CA, 1 page long (in PDF format).*
ISA/KIPO, International Search Report and Written Opinion dated Jan. 9, 2017 in Int'l Application No. PCT/US2016/056097, 15 pages.
Heinemann et al., 'Delivery of proteins to mammalian cells via gold nanoparticle mediated laser transfection', Nanotechnology, vol. 25, No. 24, Article No. 245101 (internal pp. 1-9) (2014).
Pavot et al., 'Encapsulation of Nod1 and Nod2 receptor ligands into poly(lactic acid) nanoparticles potentiates their immune properties', Journal of Controlled Release, vol. 167, pp. 60-67 (2013).
Hanson et al., 'Nanoparticulate STING agonists are potent lymph node-targeted vaccine adjuvants', The Journal of Clinical Investigation, vol. 125, No. 6, pp. 2532-2546 (Jun. 2015).
Dahiya et al., 'Nod2 downregulates TLR2/1 mediated IL1beta gene expression in mouse peritoneal macrophages', PloS One, vol. 6, Issue 11, e27828 (internal pp. 1-11) (2011).
Arita et al. "Spatially optimized gene transfection by laser-induced breakdown of optically trapped nanoparticles," American Institute of Physics, Mar. 2, 2011, vol. 98, pp. 093702-1-09370-3.
Schomaker et al. "Characterization of nanoparticle mediated laser transfection by femtosecond laser pulses for applications in molecular medicine," Journal of Nanobiotechnology, Feb. 3, 2015, vol. 13, Chapter 10, pp. 1-15.

* cited by examiner

*Primary Examiner* — Robert M Kelly
(74) *Attorney, Agent, or Firm* — Harness, Dickey and Pierce, P.L.C.

(57) ABSTRACT

Systems and methods of inducing large-scale optical transfection and generation of an immune response in target cells are presented. In preferred aspects large-scale optofection uses nanoparticles with target specific affinity moieties to generate cavitation events proximal to the cell membrane of cells to which the nanoparticles are attached, and suspended and/or dissolved cargo is so provided access into the cell. Notably, cells can be transfected in very large quantities at high viability, with the transfected cells exhibiting up-regulated immune responses.

20 Claims, 9 Drawing Sheets

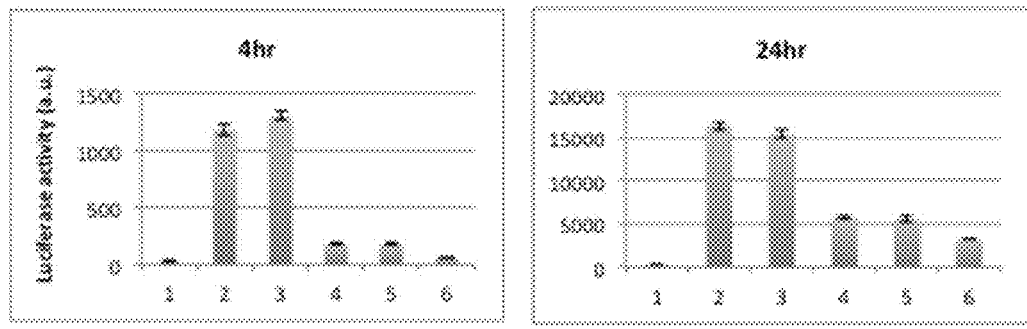

Bin Legend:
1. No treatment (no laser, no nanoparticles)
2. Nanoparticles with CD14 with laser and 10uM cGAMP
3. Nanoparticles with CD14 with laser and 1uM cGAMP
4. Nanoparticles with CD14 with laser only
5. Nanoparticles with CD14 no laser
6. cGAMP 10uM with no nanoparticles and no laser

Figure 4

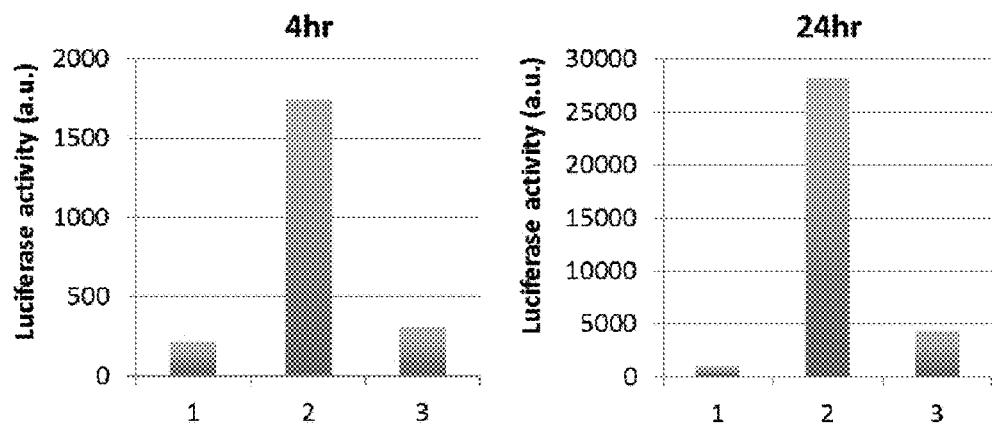

Bin Legend:
1. No BLAST treatment (no laser, no nanoparticles)
2. BLAST delivery of cGAMP at 2.5 uM cGAMP
3. Co-incubation with cGAMP at 2.5 uM cGAMP (no laser)

Figure 5

ACTIVATION OF IMMUNE-RELATED SIGNALING PATHWAYS IN CELLS VIA OPTOFECTION

This application claims the benefit of priority to U.S. provisional application having Ser. No. 62/238,652, which was filed Oct. 7, 2015.

FIELD OF THE INVENTION

The field of the invention is compositions and methods for cell treatment, especially as it relates to stimulation of immune response.

BACKGROUND

The background description includes information that may be useful in understanding the present inventive subject matter. It is not an admission that any of the information provided herein is prior art or relevant to the presently claimed inventive subject matter, or that any publication specifically or implicitly referenced is prior art.

All publications and patent application identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Rendering cancer cells 'visible' to an immune system has become a promising avenue in immune therapy and typically requires transformation or otherwise manipulating cells to increase the visibility of cancer cells to the immune system. For example, immune competent cells, and especially dendritic cells can be transformed to express recombinant cancer related proteins (e.g., neoepitopes), which typically requires bacterial, yeast, or viral gene expression systems that tend to be relatively large and therefore require dedicated delivery techniques (e.g., viral transfection, lipofection, etc.). In other examples, cancer cells can be treated with various chemicals to trigger the cells to produce surface markers that increase the visibility of cancer cells to the immune system. Unfortunately, the delivery of cargo material into cells is often problematic, particularly where delivery is to be performed at a relatively large scale while maintaining viability of the treated cells.

For example, U.S. Pat. No. 8,080,399 describes using a Bessel beam of a laser to create a pore in a cell membrane. Notably, the same beam is also required to trap or manipulate the material for introduction into the cell. Although useful for targeted delivery of material into a single cell, such approach does not scale for bulk manipulation of cells. In another example, US 2011/0111002, glutathione coated nanoparticles are employed to import glutathione into a cell. While conceptually relatively simple, such approach requires transmembrane transport of the nanoparticle, which is typically not very efficient. To increase efficiency, nanoparticles were used to generate cavitation bubbles to temporarily open cell membranes as is taught in CN 102776237. Similarly, US 2013/0113140 describes use of nanoparticles to generate a cavitation event that is triggered by laser induced breakdown of the nanoparticles. Here, the nanoparticles are optically trapped as single nanoparticles. Consequently, such methods are not suitable for large scale transfection of a relatively large number of cells.

More recently, efforts have been made toward modifying certain cells to specifically induce some form of immune response. For example, CN 103908468 teaches that cGAMP could be used to prepare injectable anti-tumor compositions. Similarly, WO 2015/077354 describes administration of stimulator of interferon genes (STING) agonists intra-tumorally. Likewise, US 2014/0329889 discloses triggering of type I interferon by increasing cyclic-di-nucleotides within a cell. However, such attempts again require transmembrane transport of the therapeutic entities and as such efficacy is relatively low. Moreover, due to the limited approaches in transfecting cells with therapeutic entities, large scale preparation of cells with an induced innate immune response have remained elusive.

Thus there remains a need for efficient delivery of therapeutic entities, and especially triggers of an innate immune response into target cells, particularly where such target cells are then employed as cellular therapeutics.

SUMMARY OF THE INVENTION

The inventive subject matter is drawn to compositions, cells, and methods of delivery of a cargo into a plurality of cells at high efficiency with high viability of the so modified cells. Most advantageously, the cells are modified to stimulate an immune response, and especially an innate immune response.

In one aspect of the inventive subject matter, the inventors contemplate a method of large-scale transfection of cells that includes a step of contacting the cells with a plurality of nanoparticles to thereby produce a nanoparticle-tagged target cells, wherein the nanoparticles have an affinity moiety that binds specifically to a marker on the target cells, and wherein the cells are disposed in a medium. In another step, a cargo material is present in or added to the medium (preferably suitable for cultivating the nanoparticle-tagged target cells), wherein the cargo material is at least one of a stimulant of an immune response, a regulatory element of an immune response, and a recombinant expression construct encoding an expressible neoepitope. In still another step, the nanoparticles on the nanoparticle-tagged target cells are excited in the medium with an electro-magnetic stimulus at an energy of at least 1 mJ to cause transient poration of the nanoparticle-tagged target cell and uptake of the cargo material into the nanoparticle-tagged target cell, wherein the step of exciting is performed at a cell density of at least $1 \times 10^4$ cells/cm2 in static medium or at a cell density of at least $1 \times 10^6$ cells/hr in moving medium. Preferably, the poration of the nanoparticle-tagged target cell and uptake of the cargo material into the nanoparticle-tagged target cell is at a viability of at least 90%.

It is generally contemplated that the plurality of nanoparticles comprise metallic nanoparticles (e.g., gold nanoparticles), and/or that the affinity moiety is a receptor ligand or an antibody or fragment thereof. Moreover, it is also contemplated that the marker on the target cells is a receptor or a neoepitope (e.g., cancer and patient-specific neoepitope), most typically characteristic of a cell type or disease. While not limiting to the inventive subject matter, it is preferred that the stimulant of the immune response comprises a STING ligand or a NOD2 ligand, and/or that the regulatory element of an immune response comprises a cytokine or a siRNA. Where desired, contemplated methods may further include a step of introducing the nanoparticle-tagged target cells into a patient after the step of exciting the nanoparticles.

Consequently, and in a further aspect of the inventive subject matter, the inventors contemplate a method of inducing an innate immune response in a cell. Such method will typically include a step of contacting the cell with a nanoparticle to thereby produce a nanoparticle-tagged target cell, wherein the nanoparticle has an affinity moiety that binds specifically to a marker on the target cell, and wherein the cell is disposed in a medium. In another step, a cargo material is introduced into or present in the medium, wherein the cargo material is a stimulant of an innate immune response. The nanoparticle on the nanoparticle-tagged target cell is then excited in the medium with an electro-magnetic stimulus at an energy sufficient to cause transient poration of the nanoparticle-tagged target cell, wherein the transient poration leads to uptake of the cargo material by the target cell to thereby form a treated target cell having induced innate immune response (e.g., interferon stimulated response).

In such methods it is generally contemplated that the marker is a marker of an immune competent cell or a marker of a cancer cell, and/or that the stimulant of the innate immune response comprises a STING ligand or a NOD2 ligand. Moreover, it is preferred that the electro-magnetic stimulus is a laser pulse from a pulsed laser or a laser pulse from a biophotonic laser-assisted cell surgery tool.

Viewed from a different perspective, the inventors therefore also contemplate a method of inducing an interferon-stimulated immune response in target cells (e.g., cancer cells) that are disposed within a heterogeneous cell population comprising non-target cells (e.g., non-cancer cells). In such methods, light absorbing nanoparticles are introduced to the cell population to thereby selectively produce nanoparticle-tagged target cells within the cell population, wherein the cell population is disposed in a medium, and wherein the light absorbing nanoparticles have an affinity moiety that binds specifically to a target in the target cells. In another step, a STING (stimulator of interferon genes) ligand and/or a NOD2 (nucleotide-binding oligomerization domain-containing protein 2) ligand is present in or introduced into the medium, and the light absorbing nanoparticles are excited via laser stimulation at an energy sufficient to cause transient poration of the nanoparticle-tagged target cells to thereby cause uptake of the at least one of the STING ligand and NOD2 ligand and to thereby stimulate the interferon-stimulated immune response in the target cells.

Most typically, the affinity moiety is a receptor ligand or an antibody or fragment thereof, and the target is a target specific to an immune competent cell or a cancer cell. Furthermore, suitable STING ligands include one or more cyclic di-nucleotides while suitable NOD2 ligands include one or more muramyl dipeptides. As noted before, it is generally preferred that the laser stimulation is performed using a laser pulse from a pulsed laser or a biophotonic laser-assisted surgery tool.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4 provides additional data that illustrate the efficiency by which optofection is able to trigger an immune response.
FIG. 5 provides additional data that illustrate the efficiency by which optofection is able to trigger an immune response via BLAST.
FIG. 6A illustrates a large scale multiwell plate transfection set-up, while
FIG. 6B illustrates a large scale flow-through transfection set-up.

DETAILED DESCRIPTION

The inventive subject matter is drawn to various systems, compositions, and methods in which cargo material can be delivered to various cells at large scale, high viability and specificity. Most advantageously, contemplated systems and methods allow for delivery of immune stimulatory compounds to trigger an immune response, and most typically an innate immune response in a mammalian cell. In particularly contemplated aspects, optofection has been shown to allow for delivery of various immune stimulatory agents to different cells at high selectivity, rate, and viability. Where the cells are autologous cancer cells of a patient, so treated cells can be administered to the same patient to thereby trigger a systemic immune response against the cancer cells. In addition, the inventors also discovered that such delivery is suitable for various plant cells, even in the presence of a cell wall, and that cargo such as small molecules, proteins, RNA, DNA, and organelles (e.g., mitochondria, chloroplasts, and a nucleus) could be delivered.

Figure 1A:
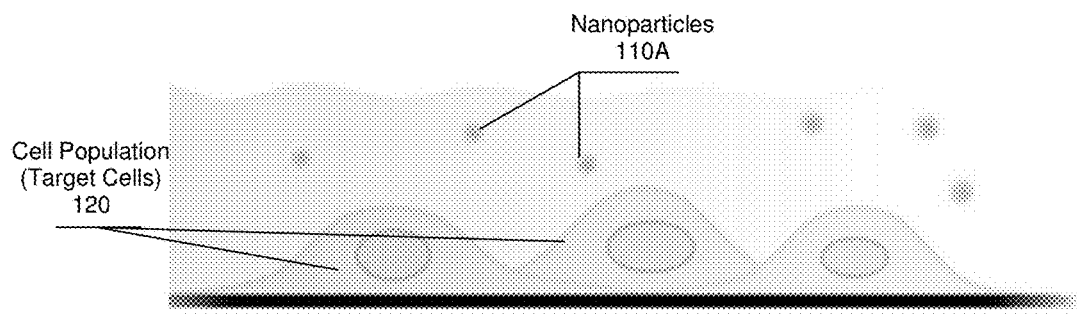
FIG. 1A schematically illustrates introduction of nanoparticles to a cell population.
Figure 1B:
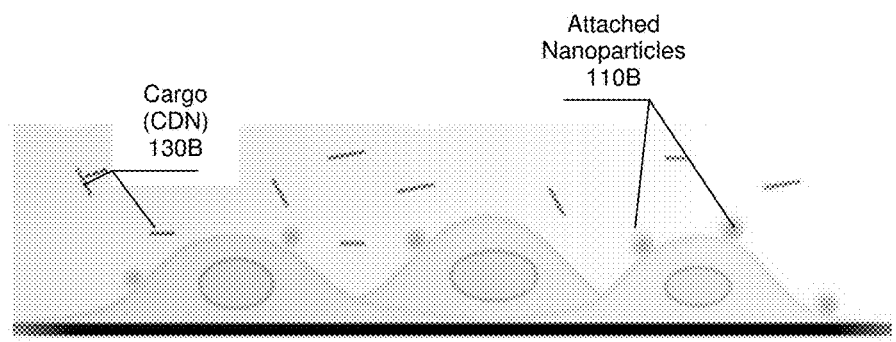
FIG. 1B schematically illustrates nanoparticles attached to target cells and cargo material in the medium surrounding cell population of FIG. 1A.
Figure 1C:
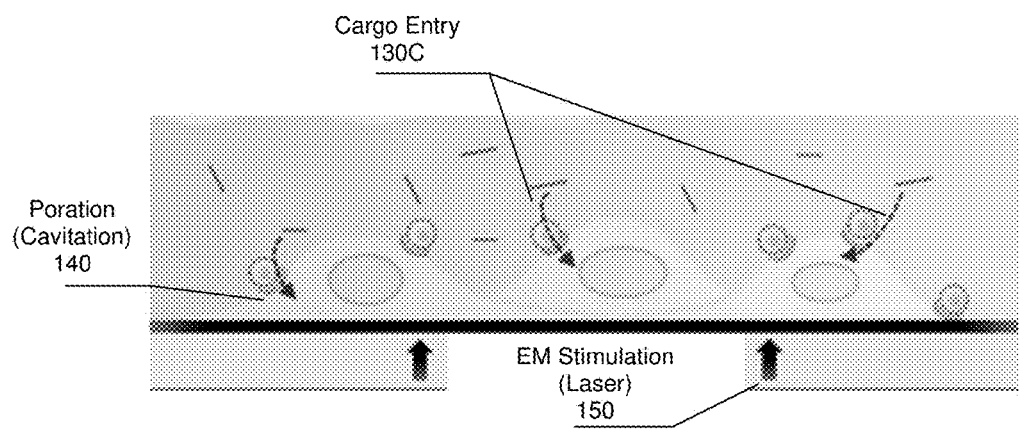
FIG. 1C schematically illustrates delivery of the cargo material into the target cells via induced poration at the attachment sites of the nanoparticles of FIG. 1B.

FIGS. 1A-1C schematically illustrate an overview of delivering immunologically relevant molecules which participate in the modulation of an immune response in target cells. In this overview, by way of example, cyclic dinucleotide CDN cargo is delivered to specific target cells using freely dissolved/dispersed cargo and nanoparticles associated with an affinity moiety that binds specifically to a marker on the target cells. Among other things, the present systems and methods advantageously allow to stimulate or otherwise activate a pathway within a target cell (preferably a tumor cell), which will induce an immune response. Once the immune response has been induced, the target cell will become 'visible' to the immune system, and the immune system can seek out and destroy the treated target cells. As a consequence, thusly treated cells will also contribute to an adaptive immune response in the patient where the treated cells are placed into the patient. For example, and as described in more detail below, STING ligands (e.g., cGAMP) can be used to activate such pathways. Moreover, the inventive subject matter is considered to include inducing an immune response in target cells of a cell population that may be a homogenous set of cells or a heterogeneous mix of different cells or cell types. For example, a homogenous set of target cells might be disposed within a lab raised culture ex vivo, while a heterogeneous mix of cells might be disposed in vivo within a patient's body where the disclosed technique can be applied to the patient's tissue as part of a treatment.

FIG. 1A illustrates a possible first step of the disclosed method. The step includes introducing (typically non-natural) nanoparticles 110A to cell population 120. Nanoparticles 110A are typically configured to attach to one or more types of target cells of cell population 110, preferably via an affinity moiety having specific binding affinity to a particular target (e.g., receptor, or extracellular portion of a membrane bound protein). For example, non-natural nanoparticle 110A could include light absorbing nanoparticles having ligands or antibodies that selectively allow the nanoparticles 110A attach to a desired cell type (see nanoparticles 110B in FIG. 1B). For example, nanoparticles 110A can include nearly any type of targeting motif including antibodies and ligands as previously mentioned as well as aptamers, antigens, affinity maturated or affinity isolated peptides (e.g., via phage display or RNA display), or other features capable of attaching to target cells.

Non-natural nanoparticles 110A could comprise one or more different materials that are considered biocompatible. In some embodiments, non-natural nanoparticles 110A include metallic nanoparticles that could be sensitive to electromagnetic energy. Such metallic nanoparticles can be comprised of gold, silver, nickel, iron oxide, zinc oxide, gadolinium, titanium oxide, or other types of metallic compounds. It should be appreciated that nanoparticles 110A could also include non-metallic nanoparticles, possibly including silicon or black carbon for example. With respect to more interesting embodiments, the nanoparticles 110A are constructed to be responsive to specific electro-magnetic stimulation. Ex vivo embodiments could include nanoparticles that would be excited by lasers while in vivo embodiments might include nanoparticles would be excited by radio frequencies (e.g., MRI, etc.). It is also contemplated that non-natural nanoparticles 110A could include magnetic dipoles allowing for greater manipulation of non-natural nanoparticles 110A via magnetic fields.

Non-natural nanoparticles 110A can vary in size depending on the target application or use. In the examples described below, the Applicants have found that gold non-natural nanoparticles 110A having an average size (e.g., average diameter, average maximum linear dimension, etc.) in the range of 10 nm to 1 um are especially suitable. In still further contemplated aspects, nanoparticles may comprise naturally occurring or synthetic materials to provide specific function or reduce immunogenicity. For example, nanoparticles could be coated with albumin or polyethylene glycol to reduce immunogenicity, while nanoparticles coated with lactoferrin could provide a transport mechanism for drugs or other therapeutic agents.

Nanoparticles 110A can be coated or otherwise tagged with one or more features so that they preferentially attach to specific target cells of cell population 110. For example, nanoparticles 110A can include antibodies targeting a variety of surface antigens (e.g., CD1, CD3, CD14, CD16, CD19, CD92, EpCam, neoepitopes, etc.) so that the nanoparticles 110A will attach to target cells in a preferential (at least 70% of all bound nanoparticles will be bound to intended target) or even selective (at least 90% of all bound nanoparticles will be bound to intended target) manner. Such an approach allows for nanoparticles 110A to be used especially in conjunction with cell population 120 having a heterogeneous mix of cell types that could have specific target cells as well as non-target cells. Thus, only the target cells, non-healthy cells for example, could be targeted for treatment. Specific target cells could include infected cells, cancer cells, blood cells, normal or healthy cells, cells of a single tissue type, embryonic cells, stem cells, cells presenting neoepitopes, etc.

In the example shown in FIG. 1A, cell population 120 is presented as an ex vivo population. It should be appreciated that cell population 120 could alternatively comprise an in vivo tissue, possibly including a tumor tissue. Further, as shown in the example and in FIGS. 2A-2C, cell population 120 could also include in vitro tissue, possibly as part of a preparation for creating treated target cells.

FIG. 1B illustrates a next step of the disclosed method, which includes introducing nucleic cargo material 130B to cell population 120 where nucleic cargo material 130B is free (e.g., dissolved or dispersed) in the sense it is external and not necessarily bound to the target cells or attached to nanoparticles 110B. Nucleic cargo material 130B (here: CDN) stimulates an immune response in the desired target cells. As a more specific example, FIG. 1B represents introducing free CDN cargo to cell population 120 where the CDN cargo (e.g., cGAMP) activates an interferon immune response in the target cells.

Cargo material 130B can take on many different forms while falling within the scope of the inventive subject matter. As mentioned previously, cargo material 130B can be presented to cell population 120 in a manner where cargo material 130B is initially free from nanoparticles 110B or the target cells. Thus, cargo material 130B can be considered as ambiently available for uptake. For example, in some embodiments, cargo material 130B composes a solution. In embodiments where cargo material 130B comprises CDNs (e.g., cGAMP, etc.) or proteins (e.g., chimeric fusion proteins such as LMP1-IPS or LMP1-TNFRSF protein fusion protein), solutions or suspensions having concentrations in the range of 1 nM to 10 uM have been found to be effective. It is also contemplated that the solution or suspension comprising cargo material 130B can also include nanoparticles 110A. Furthermore, the cargo material may be attached (covalently or non-covalently) to a solid or dissolvable carrier, or be enclosed by mono- or bilayered membrane structures (e.g., single or multilamellar vesicles).

Cargo material 130B represents a nucleic cargo (i.e., a material associated with genomic pathways) that directly or indirectly impacts a cell pathway, especially an immune response pathway. In more interesting embodiments, cargo material 130B activates an interferon immune response in the target cells (e.g., a Type I IFN response, etc.). Examples of cargo material therefore include CDNs (e.g., cGAMP, cGAS, etc.), siRNA, a peptide, a protein, an RNA sequence, a DNA sequence, a non-target cell nucleic sequence, or other types of cargo. Most preferably, cargo material comprises STING ligands (e.g., 2'3'-cGAMP, 3'3'-cGAMP, 2'2'-cGAMP, 2'3'-c-di-AMP, c-di-GMP, c-di-IMP, c-di-UMP, etc.) and MDA5/RIG-1 ligands (e.g., dsDNA, 5'pppdsRNA, poly(dA:dT), poly(I:C), etc. While immune modulation is generally a preferred effect of importing cargo into a cell, alternative cargo material can include CRISPR/Cas9 payloads capable of editing the target cells genome. On the other hand, suitable cargo material in addition to various nucleic acids (DNA, RNA, siRNA, CRISPR/Cas9 constructs, etc.) will also include larger macromolecular structures, and especially various organelles (e.g., a nucleus, mitochondria, chloroplast or other plastids, vesicles, etc.).

FIG. 1C illustrates a step by which the target cells uptake cargo material 130B. The step includes exciting attached nanoparticles 110B via electro-magnetic stimulation 150 at a sufficient energy to cause transient poration 140 of the target cell membranes, thereby causing uptake of the nucleic cargo material by the target cells, which results in treated target cells. As a more specific example, consider a scenario where attached nanoparticles 110B comprise light absorbing nanoparticles (e.g., gold, carbon black, etc.). The light absorbing nanoparticles can be excited via laser stimulation at sufficient energy (e.g., 2 mJ, 3 mJ, etc.) to cause transient poration 140, which assist in uptake of cargo 130C. Electro-magnetic stimulation 150 can be achieved through optofection, use of a laser (e.g., pulsed laser, etc.), radio frequency, BLAST, or other forms of stimulations to which the nanoparticles are responsive. In the example shown in FIG. 1C, once poration 140 occurs, cargo material 130B enters the cells and impacts the targeted pathways. Cells lacking attached nanoparticles 110B (i.e., non-target cells) remain substantially unaffected as illustrated in and evidenced by FIGS. 2A-2C. In this context, it should be appreciated that cargo entry is particularly effective with intimate contact of the nanoparticles with the target cell. Indeed, only when the nanoparticles are attached to the target cell by an affinity moiety or other non-covalent interaction will high cargo uptake occur at high viability rates.

With respect to suitable cells it is contemplated that the nature of the cell or cells is not limiting to the inventive subject matter, and that in fact all types of cells are deemed appropriate for use herein. However, especially preferred cells include suspended and adherent mammalian cells, and particularly human cells. Therefore, the tissue type of the cells may vary considerably. Likewise, it should be appreciated that the cells may be healthy cells (e.g., immune competent cells) or diseased cells (e.g., cancer cells), typically obtained from a patient. In still further contemplated aspects, the cells may also be cultivated cells that may be allogenic or autologous with respect to a patient. Moreover, it should be recognized that suitable cells need not be limited to adherent or suspended cells, but may also include cells in a tissue in vitro or even in vivo. Still further, it should be appreciated that suitable cells may also include fungal cells, mycoplasmas, and plant cells. For example, suitable plant cells will include cells or tissues isolated from a live plant or portion thereof, as well as cells from callus culture, all of which may be pretreated or used as obtained. Thus, suitable plant cells may comprise a cell wall or may be present without a cell wall (delimited only by plasma membrane). Regardless of the type and status of the cells, it should also be noted that it is generally preferred that the cells are present in a therapeutically meaningful quantity. For example, cells will typically be present and subjected to treatment as described herein in an amount of at least $10^4$ cells, $10^5$ cells, $10^6$ cells, $10^7$ cells. For example, cells may be treated in a culture plat at a density of at least $1 \times 10^4/cm^2$, at least $5 \times 10^4/cm^2$, at least $1 \times 10^5/cm^2$, or at least $1 \times 10^6/cm^2$, or may be treated as suspended cells (e.g., in a flow path or capillary) at a density of $1 \times 10^4$/ml, at least $5 \times 10^4$/ml, at least $1 \times 10^5$/ml, or at least $1 \times 10^6$/ml.

As the nature of suitable cells may vary substantially, it should be appreciated that the marker on target cell target may also vary considerably, and it is generally contemplated that all markers are suitable that are expressed and presented on the cell surface in an amount that is sufficient to allow for attachment of the nanoparticles to the cell via an affinity moiety. For example, appropriate markers may be specific for a particular cell type (e.g., tissue type), for a specific state of the cell (e.g., cancer cell, infected cell, aged cell, etc.). Of course, it should be recognized that the marker may be native to a cell or that the marker may be expressed in the cell from a recombinant nucleic acid. Still further, it should be appreciated that the marker may also be a binding moiety (e.g., antibody or fragment thereof) that has bound to a specific cell marker on the cell surface. Consequently, contemplated markers on a target cell include receptors, transporters, extracellular portions of various (trans)membrane proteins, MHC-I/II presented peptides, and recombinant proteins expressed in the target cell. Viewed from a different perspective, suitable markers include lipoproteins, glycoproteins, post-translational modified proteins, and unmodified proteins. Similarly, where the target cells are plant cells, suitable markers include those found on the plasma membrane and/or cell wall. For example, contemplated plasma membrane markers include plasma membrane cation binding proteins, plasma membrane H+ ATPase, potassium channel KAT3, aquaporins, etc., while suitable cell wall markers include α-L-fucosylated xyloglucan, 6-linked β-D-galactose oligomers that contain arabinose, methyl-esterified homogalacturonan, xylogalacturonan, arabinogalactan, etc. Antibodies to these markers are commercially available and were also published in various papers. Additionally, it is contemplated that suitable markers include those that are associated with the desired effect in the target cell. For example, where the desired effect of the target cell is stimulation of an immune response pathway using STING or RIG-1 signaling, preferred markers include CD14 or TLR or NOD receptors.

Thus, it should be recognized that suitable affinity moieties will vary considerably and that the affinity moiety will typically be a natural or synthetic binder to the marker of the target cell. For example, where the marker is a receptor, the affinity moiety may be a ligand (which may be neutral, agonist or antagonist). On the other hand, affinity moieties may also be an antibody or a fragment thereof (e.g., Fab', F(ab')$_2$, scFv, etc), or a synthetic binder that is isolated or prepared via phage display or RNA display. Further suitable affinity moieties will include lectins, aptamers, etc. Most typically, the affinity of the affinity moiety to the marker of the target cell is in the micromolar range, and typically sub-micromolar range, for example, the $K_D$ of the affinity moiety with respect to the marker is equal or less than $10^{-6}$, or equal or less than $10^{-7}$, or equal or less than $10^{-8}$, or equal or less than $10^{-9}$.

With respect to the nanoparticles it is contemplated that various materials and sized are appropriate for use herein, and especially preferred materials include those that absorb visible light, UV light, IR light, electromagnetic radiation, and microwave radiation. In addition, suitable nanoparticles may also be magnetic. However, especially preferred materials include gold and various other metals (e.g., silver, platinum, copper, etc.), inorganic materials (e.g., silica), and various organic polymers (e.g., polystyrene, possibly colored with a dye for absorption of excitation energy, latex, carbon, etc.). Typically, the size of suitable nanoparticles will be between about 1 nm and several 100 nm, and most typically between 10 nm and 300 nm. While generally spherical geometry is preferred, other shapes such as rods and irregularly shaped forms are also deemed suitable.

Moreover, it is contemplated that the nanoparticles may be coated with one or more materials, for example, to increase coupling of the nanoparticle with the affinity moiety, to reduce immunogenicity, or to provide a carrier material for additional therapeutic agents. For example, nanoparticles could be coated with albumin or polyethylene glycol to reduce immunogenicity, while nanoparticles coated with lactoferrin could provide a transport mechanism for drugs or other therapeutic agents. Moreover, chemical linking agents can be included to allow for covalent bonding of a protein or other entity to the nanoparticle (e.g., maleimide-based linker systems).

Excitation conditions of the nanoparticles will at least to some degree depend on the composition of the nanoparticles and may vary considerably in wavelength and energy. However, it is generally preferred that the excitation is performed using a pulsed laser, BLAST, electromagnetic radiation, or ultrasound. In general, it is contemplated that the energy for excitation is sub-lethal with respect to energy type. For example, suitable energies for laser pulses will typically between 0.1 nJ and 100 mJ, for a duration of between a few fs and several milliseconds, and more typically between 100 fs and 100 µs. It is still further contemplated that the excitation will be directed through a transparent material into the medium. For example, where the cells are suspended or flow through a capillary or tube, excitation will be through the capillary or tube. Similarly, where the cells are disposed in a dish, flask, or multiwall plate, the excitation will typically be through the wall of the container. However, excitation through the medium is also contemplated. Moreover, it is further contemplated that the excitation beam will be wider than a single cell to so allow excitation of a larger number of cells (e.g., at least 2, at least 10, at least 50, at least 100, at least 1,000) in a single illumination. Therefore, it should be appreciated that the excitation will be performed in medium, typically isotonic and with nutrients, most typically in culture medium. Alternatively, excitation may also be performed in situ in a tissue, and it is generally preferred that the tissue is then at least temporarily covered with a medium. Most typically, poration under such conditions will be transient and not affect the viability of the majority of the cells. Viewed from a different perspective, poration will be sufficiently short such as to avoid leakage of a cell and/or loss of electrochemical potentials to a degree that adversely affects viability and/or downstream cell division.

The ratio of nanoparticles to cells is typically such that nanoparticles are in excess over cells, for example, at least 2:1, at least 5:1, at least 10:1, at least 100:1, at least 1000:1 to so ensure contact of substantially all targeted cells (e.g., at least 90%, more typically at least 95%, most typically at least 98%) with the nanoparticles. Likewise, it is contemplated that the cargo concentration can vary as well, but is typically at least 1 nM, at least 10 nM, at least 100 nM, at least 1 µM, at least 10 µM, or at least 100 µM to ensure presence of the cargo in a meaningful concentration proximal to the transient poration.

Based on the inventors' observations, viability after excitation is at least 85%, at least 90%, at least 94%, or at least 98%, with at least 70%, at least 75%, at least 80%, at least 90% of all cells having taken up cargo. Therefore, it is contemplated that cells can be administered to a mammal for treatment. Typically, where cells are administered to a patient after cargo uptake, the cells will be autologous (e.g., cancer or immune competent cells), but allogenic (modified NK92 cells) are also deemed suitable for use herein.

Consequently, it should be appreciated that the inventive subject matter provides apparatus, systems and methods in which one can leverage optofection to deliver ligands which modulate immune signaling in live cells or modulate a downstream immune response. These ligands can be pathogen associated molecular patterns (PAMPs), disease associated molecular patterns (DAMPS), second messengers like cyclic di-nucleotides (CDNs), nucleic acids, or proteins to a cell. For example, one aspect of the inventive subject matter includes a method of inducing an immune response in a target cell population. The disclosed methods include introducing non-natural (e.g., manmade, etc.) nanoparticles to the cell population. In some embodiments, the cell population can include a heterogeneous mix of cell types. The nanoparticles can be constructed to include ligands or antibodies (e.g., CD8, CD14, CD16, etc.), which allow the nanoparticles to preferentially attach to target cells within the cell population relative to non-target cells. The disclosed method further includes introducing a nucleic cargo material (e.g., CDNs, cGAMP, siRNA, a peptide, a protein, a fusion protein, etc.) to the cell population and external to the target cells. The cargo material includes material that can stimulate an immune response in the targets and can be introduced via a solution to the cell population. The method also includes exciting the nanoparticles via electromagnetic stimulation, a laser for example, at a sufficient energy to cause the nanoparticles attached to the target cell to initiate poration in the target cell membranes. The poration allows the target cells to uptake the nucleic cargo material.

Yet another aspect of the inventive subject matter includes a method of inducing an interferon immune response in specific target cells. Similar to the previous method, exemplary methods including introducing light absorbing nanoparticle (e.g., metallic, nonmetallic, etc.) to a cell population where the light absorbing nanoparticles are configured to preferentially attach to a specific set of target cells in the population over other non-target cells. The method continues by introducing free CDN cargo (e.g., cGAMP in a solution, etc.) to the cell population where the CDN cargo is substantially free within the solution and free (i.e., not bound) to the target cells or the light absorbing nanoparticles. The CDN cargo is configured to activate an interferon immune response in the specific target cells. The method further includes exciting or otherwise stimulating the light absorbing particles via laser stimulation at a sufficient energy to cause the light absorbing nanoparticle to induce poration in cell membranes of the specific cells to which the light absorbing nanoparticles are attached. The poration thereby causes the target cells to uptake the free CDN cargo, which results in treated cells that are induced to exhibit an interferon immune response.

Of course, it should be appreciated that the systems and methods contemplated herein are suitable for cargo other than CDNs, particularly in the context of immune stimulation. For example, the cargo may comprise peptides or nucleic acids encoding peptides in which an immunostimulator intracellular signaling peptide is fused directly or indirectly to a peptide that leads to multimerization into complexes of multiple (e.g., three or more) units, and where the intracelluar signaling peptide is present in a complex of multiple (e.g., three or more) units to so stimulate an immune response. Representative examples of such peptides and nucleic acids encoding such peptides are disclosed in US 2013/0039942, WO 2014/039961, EP 2550298 B1, and US 2015/0159136.

Therefore, especially preferred signaling peptides include Latency Membrane Protein 1 (LMP1) fused with CD40, in which the multimerizing properties of LMP1 are employed to amplify signaling effects of CD40. Of course, it is noted that various other constructs with the same or similar pattern may be used. For example, CD40 may be replaced with 4-1BB, OX40, CD27, or other TNF receptor superfamily members, including Fas, lymphotoxin beta receptor (LTBR), nerve growth factor receptor (NGFR), Tumor necrosis factor receptor superfamily member 1A (TNFRSF1A), Tumor necrosis factor receptor superfamily member 1B (TNFRSF1B), Tumor necrosis factor receptor superfamily member 4 (TNFRSF4), Tumor necrosis factor receptor superfamily member 8 (TNFRSF8), Tumor necrosis factor receptor superfamily member 9 (TNFRSF9), Tumor necrosis factor receptor superfamily member 10A (TNFRSF10A), Tumor necrosis factor receptor superfamily member 10B (TNFRSF10B), Tumor necrosis factor receptor superfamily member 10D (TNFRSF10D), Tumor necrosis factor receptor superfamily member 11A (TNFRSF11A), Tumor necrosis factor receptor superfamily member 12A (TNFRSF12A), Tumor necrosis factor receptor superfamily member 13B (TNFRSF13B), Tumor necrosis factor receptor superfamily member 13C (TNFRSF13C), Tumor necrosis factor receptor superfamily member 14 (TNFRSF14), Tumor necrosis factor receptor superfamily member 17 (TNFRSF 17), Tumor necrosis factor receptor superfamily member 18 (TNFRSF 18), Tumor necrosis factor receptor superfamily member 19 (TNFRSF 19), Tumor necrosis factor receptor superfamily member 21 (TNFRSF21), and Tumor necrosis factor receptor superfamily member 25 (TNFRSF25). Likewise, signaling pathways other than CD40 signaling pathways may be activated by adding a pathway member (and typically an activating pathway member) to the construct. For example, alternative pathways include STING pathway, RIG-1 pathway, TLR pathways, NOD pathways, apoptosis pathways, etc.

EXPERIMENTS

Figure 2A:
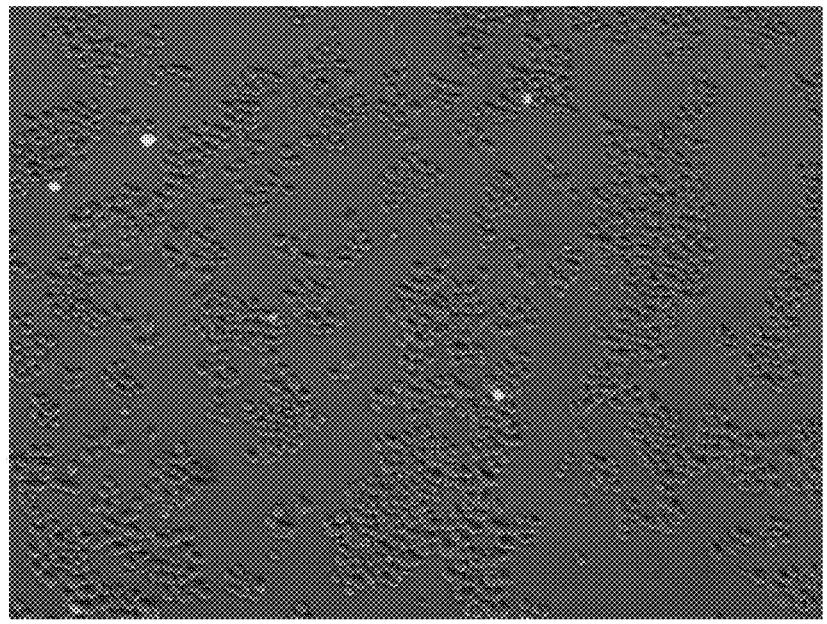
FIG. 2A is a photomicrograph after free cyclic dinucleotides (CDNs) and nanoparticles lacking ligands have been introduced to a cell population without laser stimulation; little to no transfection has occurred.
Figure 2B:
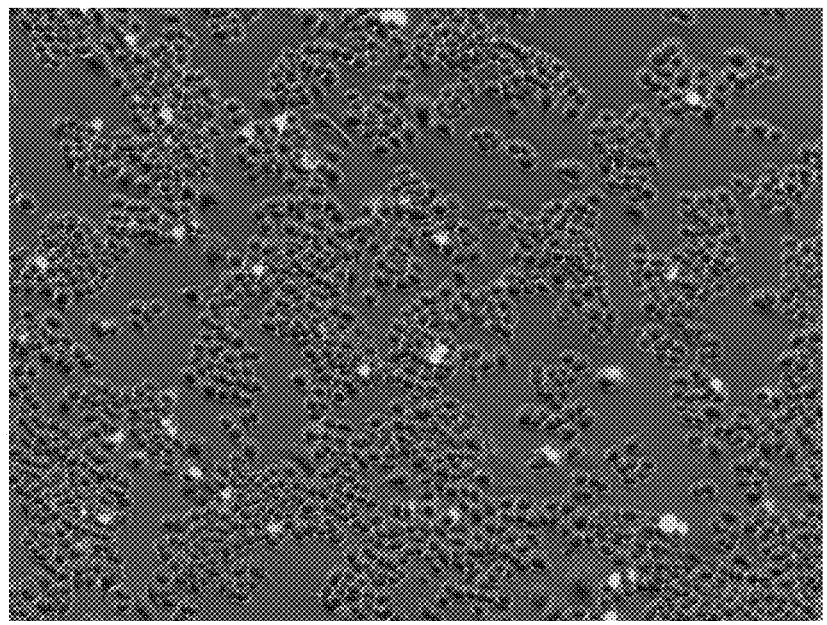
FIG. 2B is a photomicrograph after free CDNs and nanoparticles lacking ligands have been introduced to a cell population with a 3 mJ laser pulse; only negligible transfection has occurred.
Figure 2C:
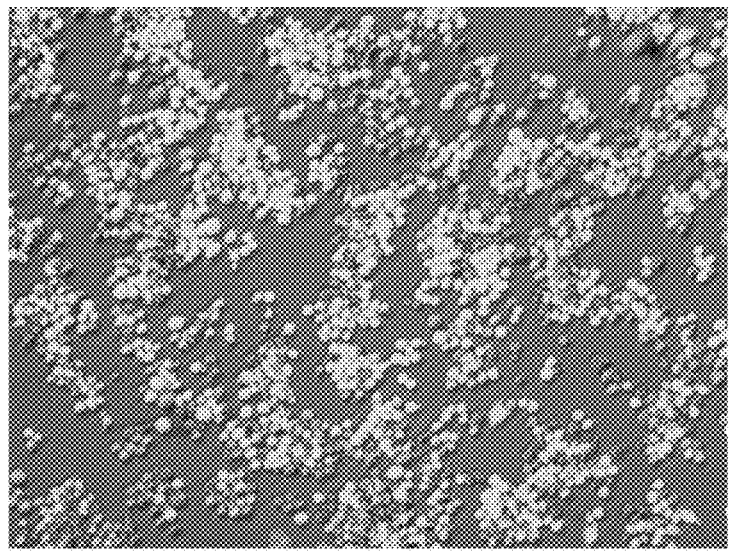
FIG. 2C is a photomicrograph after free CDNs and nanoparticles having CD14 ligands have been introduced to a cell population with a 2 mJ laser pulse; substantial transfection has occurred.

FIGS. 2A-2C illustrate experimental evidence indicating the validity of the disclosed techniques though the use of RAW-Lucia® ISG cells that express luciferase when a Type I IFN response pathway is activated (see FIG. 3) by a CDN. If target cells successfully uptake the CDN, cGAMP in these experiments, the target cells exhibit luciferase as evidenced by green indicators in the figures.

FIG. 2A represents an experiment where gold nanoparticles lacking target cell ligands (here ligand for CD145) and cGAMP cargo material are introduced to the cell population. No electro-magnetic stimulation is applied. FIG. 2A illustrates very little or negligible luciferase expression as can be seen by lack of fluorescence on the vast majority of cells, indicating no immune response has been induced under the current conditions.

FIG. 2B represents an experiment where gold nanoparticles lacking target cell ligands (ligand for CD14) and cGAMP cargo material are introduced to the cell population. In this experiment, the nanoparticles were exposed to 3 mJ pulsed laser. In this experiment, some cells express luciferase, but not in an effective about. The luciferase expression in FIG. 2B is considered to be present in response to random proximity of the gold nanoparticles to cells when the gold nanoparticles are excited by the laser.

FIG. 2C represents an experiment where gold nanoparticles having a CD14 ligand and cGAMP cargo material are both introduced to the cell population. In this case, the nanoparticles attach to the target cells. Once exposed to a 2 mJ pulsed laser, nearly all cells express luciferase indicating that the target cells have been induced to activate the Type I IFN immune response. It should be particularly noted that substantially all cells retained viability and that cargo uptake and downstream activation of the STING pathway was effected in the vast majority of cells.

Figure 3:
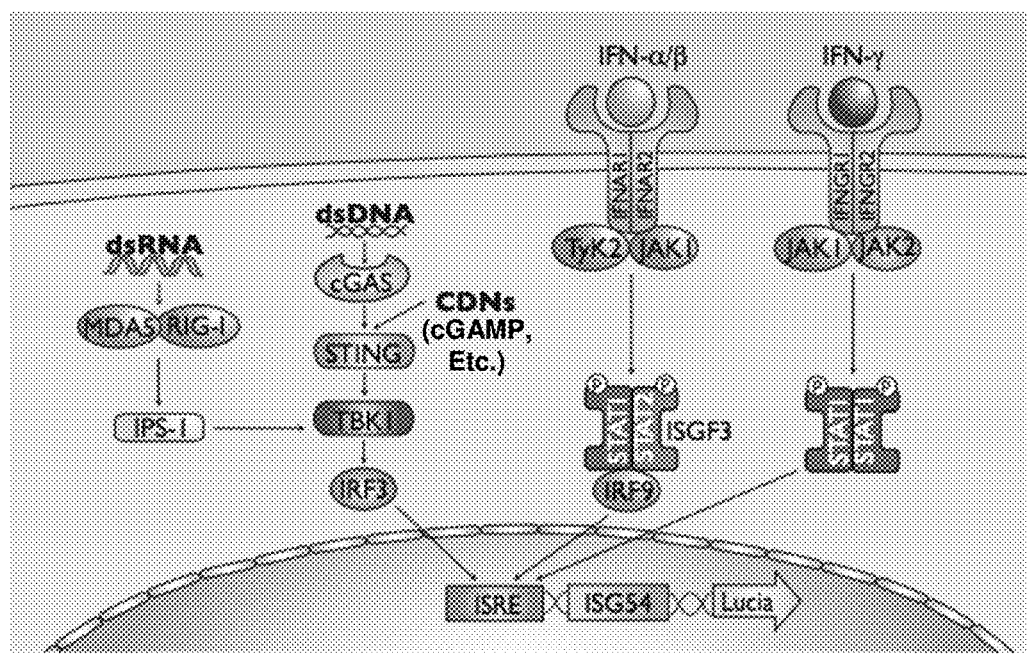
FIG. 3 is a schematic illustration of RAW-Lucia™ ISG cell line pathways through which CDNs induce an immune response that triggers luciferase production.

The immune response induced in the experiments shown in FIGS. 2A-2C is evidenced by production of luciferase in specifically targeted cells. A mentioned previously, the specifically target cells selected for the experiments were RAW-Lucia™ ISG cells commercially available from InvivoGen® (see URL www.invivogen.com/raw-lucia-isg). The RAW-Lucia cells express luciferase gene (Lucia) through various IFN-stimulated response elements (ISRE) as indicated in FIG. 3. Thus, when an IFN response is stimulated, the cells express the luciferase gene. Of specific note, when CDNs are introduced to the RAW-Lucia cells, the IFN response is activated causing expression of the luciferase gene. Therefore, FIG. 2C clearly provides evidence via substantial luciferase expression that the disclosed technique of causing a cell to uptake CDNs (e.g., cGAMP, etc.) via externally generated poration is capable of inducing an immune response. Such result is not necessarily predictable as laser excitation and concomitant cavitation events may damage or interfere with signal transduction events.

Although the experiments focused on inducing an immune response via introducing free cGAMP to the target cells, the inventive subject matter is considered to include inducing an immune response via other routes as well. Other intermediary molecules (e.g., nucleic sequences, RNA, small molecules, inhibitors, promoters, ligands, antigens, genes, siRNA, etc.) which can participate in an immune response signally pathway could also be delivered via the disclosed techniques. Still further, the immune response is not considered restricted to an IFN response. Rather, the disclosed techniques are considered advantageous and useful in stimulating any immunological pathway, innate or adaptive responses, that can be modulated by delivered cargo molecules.

FIG. 4 provides further experimental evidence with respect to the efficiency of cargo delivery to the specific target cells. The two charts show the relative luciferase activity of RAW-Lucia target cells four hours after treatment and 24 hours after treatment under different treatment configurations.

Treatment configuration 1 represents a cell population having no treatment where no nanoparticles and no laser are introduced to the RAW-Lucia cell population. As can be seen in both charts, the Treatment 1 cell population exhibited negligible luciferase activity indicating no immune response.

Treatment configuration 2 represents a cell population treated with CD14 ligand coated gold nanoparticles and a 10 uM cGAMP solution. A laser was used to excite the nanoparticles, which resulted in significant uptake of the cGAMP as evidenced by the significant luciferase activity for Treatment 2 in both the charts.

Treatment configuration 3 is similar to treatment configuration 2 with the exception that a 1 uM cGAMP solution was introduced to the cell population rather than a 10 uM cGAMP solution. Interestingly, the luciferase activity for Treatment 3 is fairly similar to Treatment 2, which indicates that the disclosed technique is also quite effective for small concentrations of CDNs.

Treatment configuration 4 includes treating the target cells with just nanoparticles coated with CD14 ligand followed by application of laser stimulation. Some luciferase activity is observed, but at significantly reduced levels relative to Treatments 2 and 3.

Treatment configuration 5 is similar to Treatment 4, although lacking laser stimulation. It is noted that both Treatments 4 and 5 exhibit similar low level luciferase activity; both well below Treatments 2 and 3.

Treatment configuration 6 includes treating the cell population with just a 10 uM cGAMP solution without nanoparticles or application of laser stimulation. Treatment 6 also exhibited a reduced level of luciferase activity.

Clearly, Treatments 2 and 3 indicate the disclosed techniques provide for fast, efficiently delivery of nucleic cargo delivery for inducement of an immune response.

FIG. 5 provides further experimental evidence with respect to the efficiency of cargo delivery to the specific target cells with respect to using a biophotonic laser-assisted surgery tool (BLAST, as described in Nature Methods 12, 439-444 (2015)). The two charts of FIG. 5 show the relative luciferase activity of RAW-Lucia target cells four hours after treatment and 24 hours after treatment under three different treatment configurations.

Treatment configuration 1 represents a control group where the cell population is not treated in order to provide a base line result.

Treatment configuration 2 leverages BLAST where the cell population is bathed in a 2.5 uM cGAMP solution. In both the 4 hour case and 24 hour case, there is significant luciferase activity indicating that the target cells executed strong up take of cGAMP.

Treatment configuration 3 includes co-incubation of the cell populations with a 2.5 uM cGAMP solution. However, the cell population is not exposed to laser stimulation via BLAST.

Treatment configuration 2 clearly illustrates that delivery of cyclic dinucleotide cargo can be achieved via BLAST. Further, it should be appreciated that the inventive subject matter is considered to include combining BLAST with use of nanoparticles as discussed above.

It should be appreciated that FIG. 5 illustrates the efficacy of a method of inducing an interferon response in specific target cells, including target cells within a heterogeneous cell population. Free cyclic di-nucleotide cargo (i.e., cGAMP in the scenario of FIG. 5) was introduced to the cell population such that the cGAMP remained external to the target cells in a 2.5 uM solution. Specific target cells can be identified for optofection, possibly via image recognition techniques (e.g., SIFT, DOG, DAISY, edge detection, SURF, FREAK, BRISK, etc.) or through nanoparticle tagging as described previously. Nano-cavitation bubbles are induced proximate to the specific target cells via laser stimulation (e.g., BLAST, etc.) at sufficient energy to cause poration in the target cells. The target cells are then induced to up take the cargo via the poration. In some embodiments, the poration can be achieved through excitation of nanoparticles attached to the target cells as described previously.

Figure 6A:
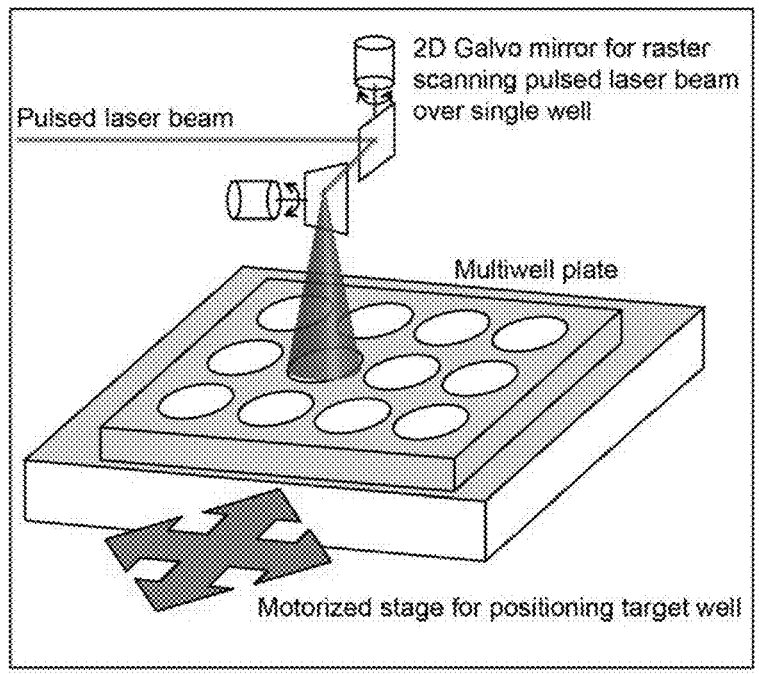
FIGS. 6A and 6B are schematic illustrations of optofection devices according to the inventive subject matter.
Figure 6B:
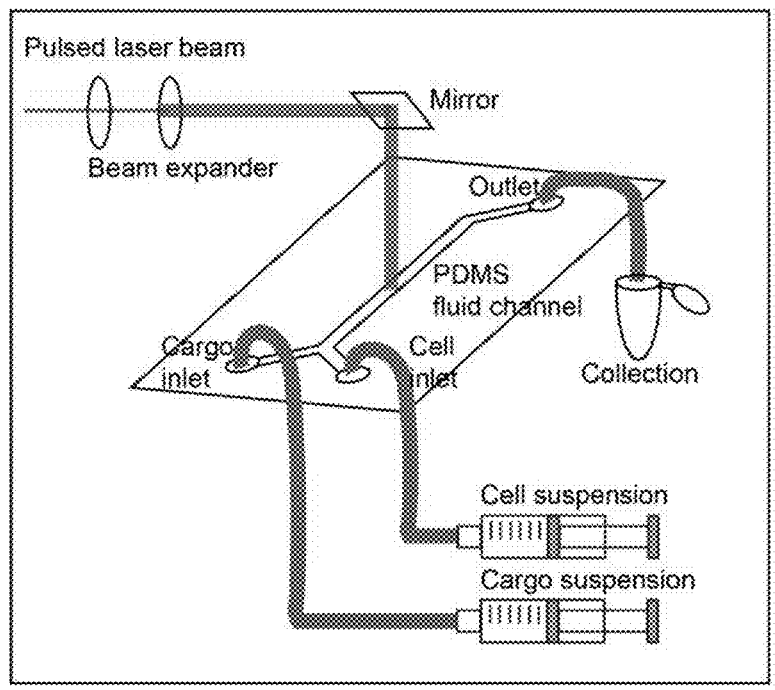

FIGS. 6A and 6B provide exemplary optofection devices that enable large-scale transfection of cells that are either placed in culture (adherent or in suspension). Here, as can be seen from FIG. 6A, a pulsed laser beam is scanned across substantially the entire area (i.e., at least 90%) of a well in a multiwall plate to so deliver energy to the nanoparticles. Movement of the plate on a stage typically assists beam steering with a mirror assembly. Of course, where desired, the laser beam can also be spread to substantially cover the entire area of the microwell. Alternatively, as shown in FIG. 6B, optofection can also be performed on-line in a microfluidic device in which cargo fluid and cell suspension are combined and flow through a path that is then irradiated with the pulsed laser beam. Of course, it should be noted that the nanoparticles may be present in the cell suspension and/or in the cargo fluid. Using such device, cells can be transfected at a very high yield and viability.

Figure 7:
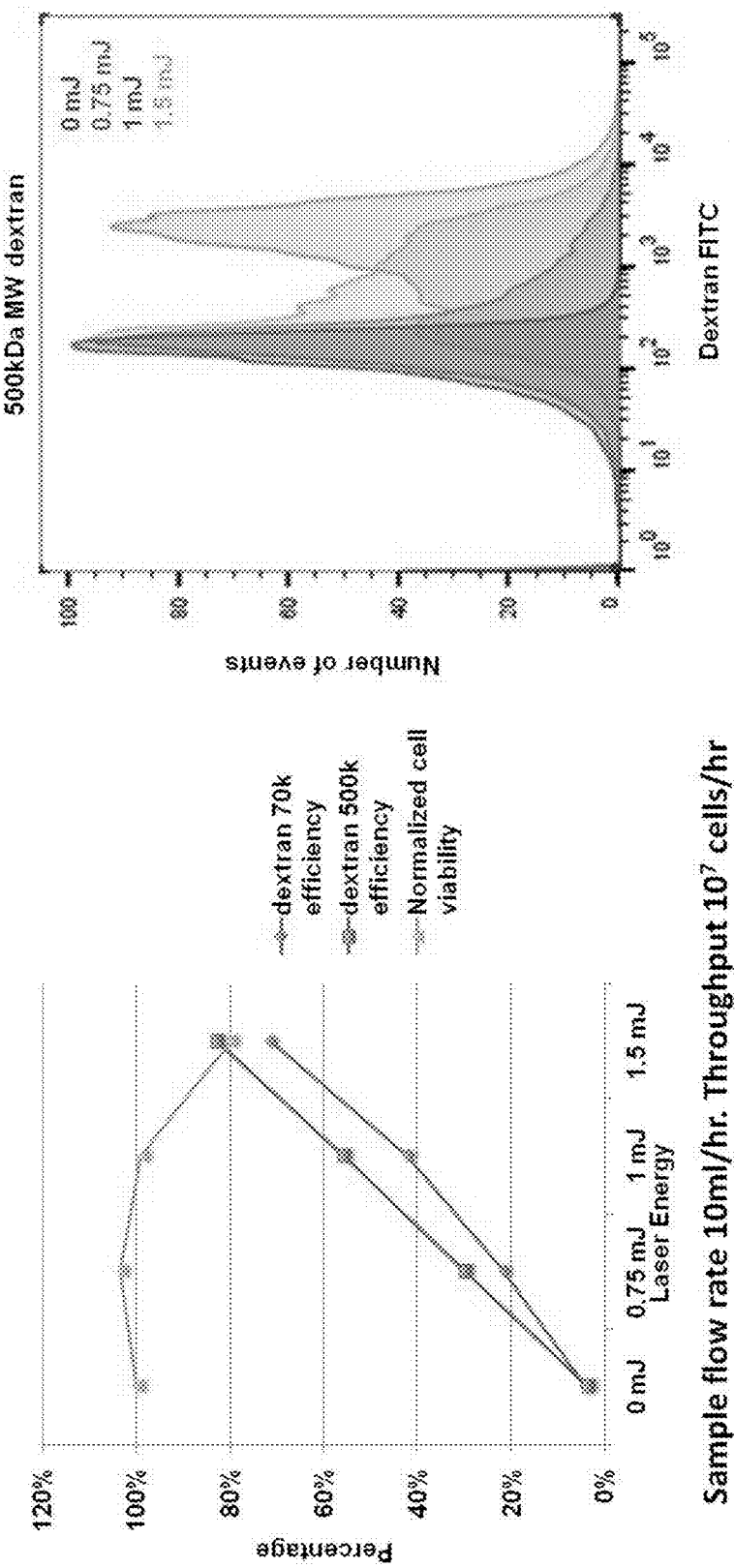
FIG. 7 shows exemplary graphs depicting experimental results for a large scale flow-through transfection set-up.
Figure 8:
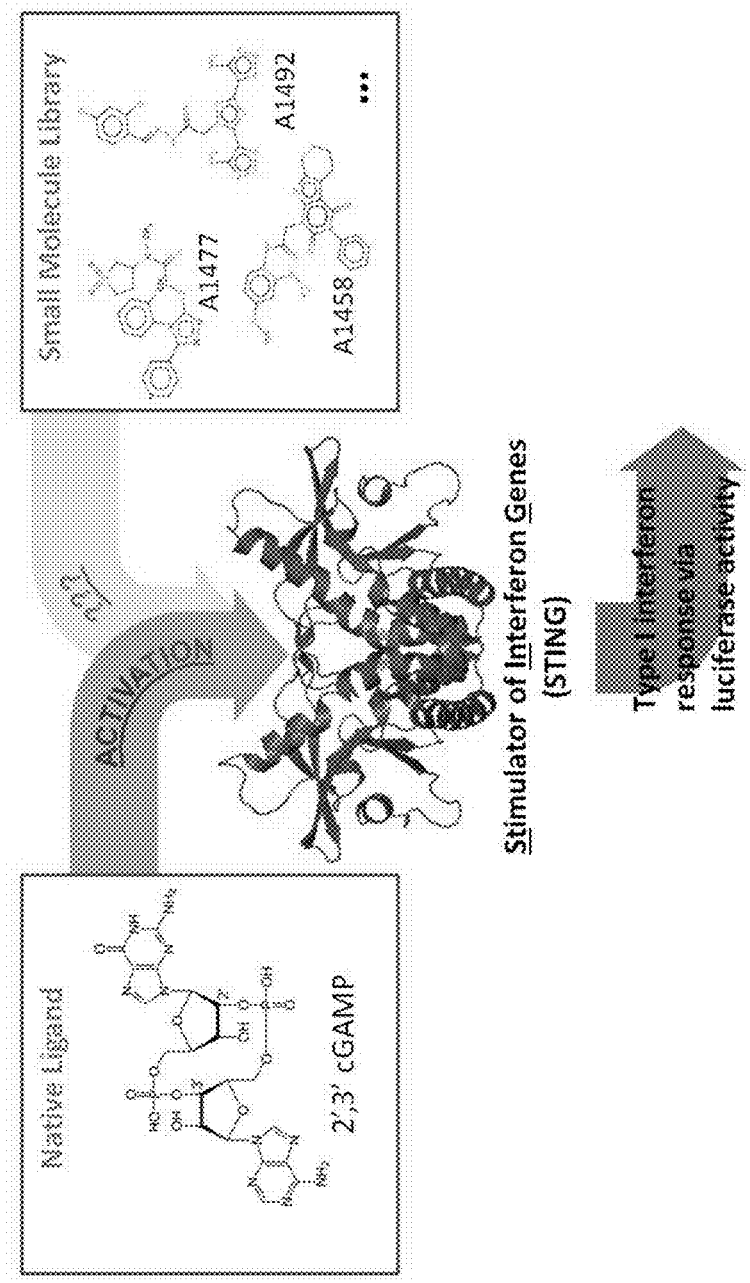
FIG. 8 depicts an exemplary set-up suitable for screening for compounds activating the STING pathways using large scale multiwell plate transfection set-up.
Figure 9:
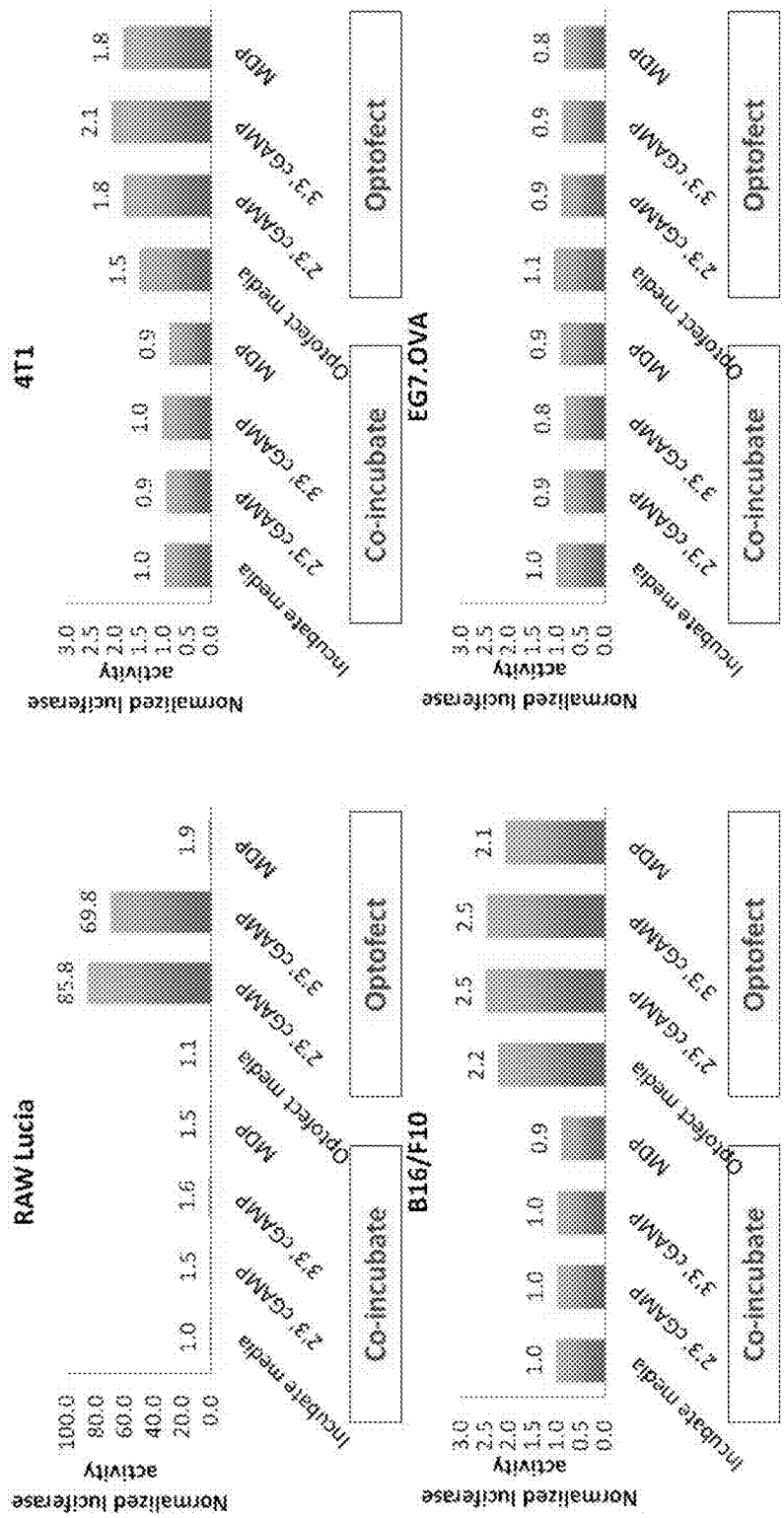
FIG. 9 shows exemplary results comparing optofection of various PRR ligands with co-incubation in different murine tumor cell lines.
Figure 10:
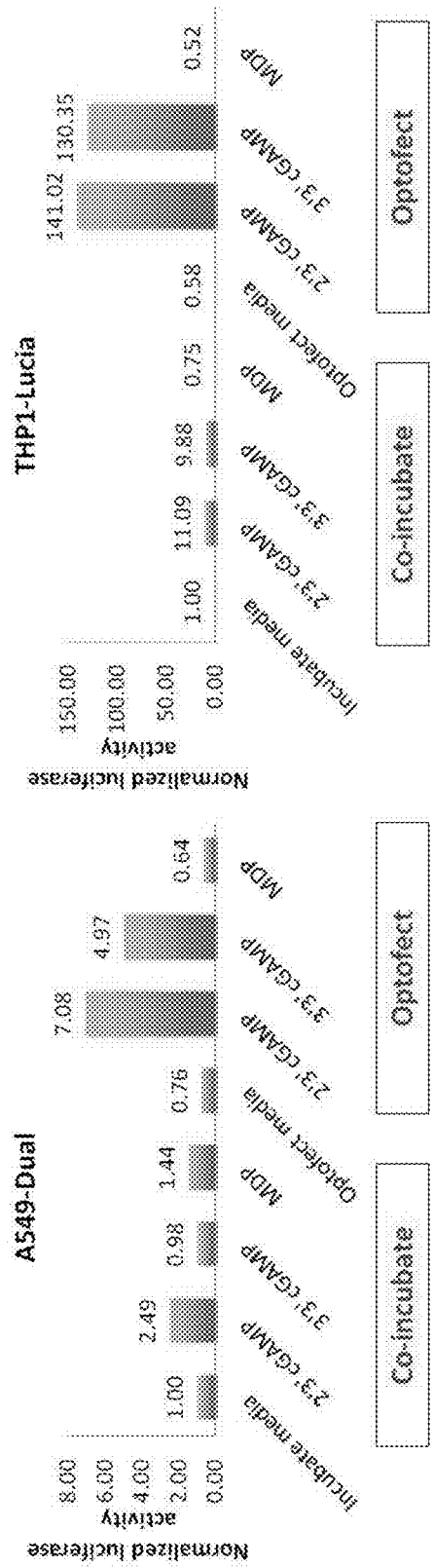
FIG. 10 shows exemplary results comparing optofection of various PRR ligands with co-incubation in different human tumor cell lines.

For example, FIG. 7 shows transfection results for haNK cells (human high affinity NK cells with high affinity CD16 receptor, commercially available from NantKwest, 9920 Jefferson Blvd., Culver City, Calif. 90232) using the flow arrangement of FIG. 6B at a flow rate of 10 mL per hour using two different sized dextran polymers as indicated and FITC as the fluorescence label. As is readily apparent, even relatively large complexes of 500 kDa are taken up at relatively high yield, with substantially complete update at an energy delivery of 1.5 mJ. The inventors therefore contemplate that using such high transfection efficiency a large number of cells can be transfected in a multiwall plate format as seen ion FIG. 6A to screen for compounds in which the cell has a reporter system (native or recombinant). In the example of FIG. 8, the cell system is a cell that has an innate STING immune response pathway that is recombinantly modified to express luciferase upon activation of the STING pathway. Of course, it should be recognized that numerous pathway activations other than STING pathway activation can be assessed. For example, FIG. 9 exemplarily shows the results of optofection of various mouse tumor cell lines (all having a luciferase gene reporter system as seen in FIG. 3) with a selection of known STING and NOD2 activators. Here, murine RAW Lucia cells, 4T1 cells, B16/F10 cells, and EG7.OVA cells were transfected and luciferase activity monitored. Clearly, all of the tested murine tumor cells were able to be transfected with various STING and NOD2 ligands and exhibited strong luciferase response to the STING and NOD2 stimulators. Notably, co-incubation without optofection did not produce any appreciable different over control. Similarly, several human cancer cell lines (A549-Dual, THP-Lucia) with luciferase gene reporter system were subjected to optofection and the results are shown in FIG. 10. Once more, as can be seen from the results, optofection was able to stimulate a substantial immune reaction as evidenced by luciferase activity.

An astute reader will appreciate numerous possible advantageous applications of the disclosed subject matter, all of which are considered to fall within the scope of the inventive subject matter. Consider a cancer treatment for example. The disclosed techniques of leveraging optofection can be used to construct one or more cancer vaccines by delivering STING ligands, cGAMP, or other molecule into tumor cells. The tumor cells would then become immunogenic and naturally susceptible to a patients natural immune system. When patients have a weakened immune system, their immune system can be bolstered via administration of natural killer cells (e.g., NK92, etc.) that are constructed to be responsive to the induced immune response.

Yet another contemplated application of the inventive subject matter includes delivering tumor antigen into antigen-presenting cells. Such an approach is advantageous because it the antigen-presenting cells will then induce an anti-tumor immune response or aid in trigger tumor-specific cytotoxic T-cells. Still further, the inventive subject matter can also be used to deliver genes, siRNA, or other molecules (e.g., chimeric proteins) to module gene expression. Through such modulation, the immune response can also be modulated or otherwise controlled. For example, immune response pathways, and especially STING pathways, TLR4 dependent pathways, MIF dependent pathways, IMD related pathways, JAK/STAT dependent pathways, etc. It should be appreciated that such modulation can include inhibiting pathways, enhancing pathways, or otherwise effecting one or more pathways associated with a desired immune response. Most preferably, however, pathway activity is enhanced by optofection with at least one of a pathway activator (e.g., STING or NOD2 ligand), a cytokine, a immune stimulator (LMP1 fusion protein, and especially LMP-TNFRSF (tumor necrosis factor receptor superfamily protein) or LMP-IPS 1 (interferon-beta promoter stimulator 1)), a neoepitope, or a cancer associated or cancer specific antigen.

In a similar manner, it should be appreciated that the systems and methods provided herein are also suitable for transfection or other modification of plant cells, which may or may not have a cell wall. Thus, plant cells or protoplasts may be provided as isolated cells or within the context of a tissue or culture (e.g., as explant or callus culture). Once obtained, it is typically preferred that the plant cells are suspended or placed into a liquid medium. Immobilization of the nanoparticles is then performed as for non-plant cells already described above, typically using antibody-associated nanoparticles or nanoparticles with high affinity to the cell wall (e.g., modified with noncatalytic carbohydrate-binding modules of enzymes that modify complex carbohydrates). The so bound nanoparticles are then subjected to laser pulses as noted before to generate bubble cavitation with sufficient strength to generate transient pores through both the plant cell wall and cell membrane simultaneously, and the cargo is then delivered into plant cell through diffusion across the plasma membrane and/or cell wall.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of large-scale transfection of cells, comprising:
  contacting the cells with a plurality of nanoparticles to thereby produce nanoparticle-tagged target cells, wherein the nanoparticles have an affinity moiety that binds specifically to a marker on the target cells, and wherein the cells are disposed in a medium;
  introducing a cargo material into the medium, wherein the cargo material is at least one of a stimulant of an immune response, a regulatory element of an immune response, and a recombinant expression construct encoding an expressible neoepitope;
  exciting the nanoparticles on the nanoparticle-tagged target cells in the medium with an electro-magnetic stimulus at an energy of at least 1 mJ to cause transient poration of the nanoparticle-tagged target cells and uptake of the cargo material into the nanoparticle-tagged target cells at a viability of at least 90%;
  wherein the step of exciting is performed at a cell density of at least $1 \times 10^4$ cells/cm$^2$ in static medium or at a cell density of at least $1 \times 10^6$ cells/hr in moving medium.

2. The method of claim 1 wherein the plurality of nanoparticles comprise metallic nanoparticles.

3. The method of claim 1 wherein the affinity moiety is a receptor ligand or an antibody or fragment thereof.

4. The method of claim 1 wherein the marker on the target cells is a receptor or a neoepitope.

5. The method of claim 1 wherein the medium comprises a culture medium suitable for cultivating the nanoparticle-tagged target cells.

6. The method of claim 1 wherein the stimulant of an immune response comprises a STING ligand that comprises one or more cyclic di-nucleotides or a NOD2 ligand that comprises one or more muramyl dipeptides.

7. The method of claim 1 wherein the regulatory element of an immune response comprises a cytokine or a siRNA.

8. The method of claim 1 wherein the neoepitope is a cancer and patient-specific neoepitope.

9. The method of claim 1 wherein the viability of the nanoparticle-tagged target cells is at least 94%.

10. The method of claim 1 further comprising a step of introducing the nanoparticle-tagged target cells into a patient after the step of exciting the nanoparticles.

11. The method of claim 1, wherein the electro-magnetic stimulus is a laser pulse from a pulsed laser or a laser pulse from a biophotonic laser-assisted cell surgery tool.

12. A method of inducing an innate immune response in a cell, comprising:
  contacting the cell with a nanoparticle to thereby produce a nanoparticle-tagged target cell, wherein the nanoparticle has an affinity moiety that binds specifically to a marker on the target cell, and wherein the cell is disposed in a medium;
  introducing a cargo material into the medium, wherein the cargo material is a stimulant of an innate immune response;
  exciting the nanoparticle on the nanoparticle-tagged target cell in the medium with an electro-magnetic stimulus at an energy sufficient to cause transient poration of the nanoparticle-tagged target cell and uptake of the cargo material into the nanoparticle-tagged target cell at a viability of at least 90% for a population of nanoparticle-tagged target cells;
  wherein the transient poration leads to uptake of the cargo material by the target cell to thereby form a treated target cell having induced innate immune response.

13. The method of claim 12, wherein the marker is a marker of an immune competent cell or a marker of a cancer cell.

14. The method of claim 12, wherein the stimulant of the innate immune response comprises a STING ligand that comprises one or more cyclic di-nucleotides or a NOD2 ligand that comprises one or more muramyl dipeptides.

15. The method of claim 12, wherein the induced innate immune response is an interferon stimulated response.

16. A method of inducing an interferon-stimulated immune response in target cells within a heterogeneous cell population comprising:
    introducing light absorbing nanoparticles to the cell population to thereby selectively produce nanoparticle-tagged target cells within the cell population;
    wherein the cell population is disposed in a medium, and wherein the light absorbing nanoparticles have an affinity moiety that binds specifically to a target in the target cells;
    introducing at least one of a STING (stimulator of interferon genes) ligand that comprises one or more cyclic di-nucleotides and a NOD2 (nucleotide-binding oligomerization domain-containing protein 2) ligand that comprises one or more muramyl dipeptides to the medium; and
    exciting the light absorbing nanoparticles via laser stimulation at an energy sufficient to cause transient poration of the nanoparticle-tagged target cells to thereby cause uptake of the at least one of the STING ligand and NOD2 ligand and to thereby stimulate the interferon-stimulated immune response into the target cells at a viability of at least 90%.

17. The method of claim 16, wherein the affinity moiety is a receptor ligand or an antibody or fragment thereof, and wherein the target is a target specific to an immune competent cell or a cancer cell.

18. The method of claim 16, wherein the STING ligand is a cyclic di-nucleotide and wherein the NOD2 ligand is a muramyl dipeptide.

19. The method of claim 16 wherein the laser stimulation is performed using a biophotonic laser-assisted surgery tool.

20. The method of claim 16, wherein the target cells are cancer cells, and wherein the heterogeneous cell population comprises non-cancer cells.

* * * * *